(12) United States Patent
Barge et al.

(10) Patent No.: US 10,836,710 B2
(45) Date of Patent: Nov. 17, 2020

(54) MECHANOCHEMICAL SYNTHESIS OF RADIOGRAPHIC AGENTS INTERMEDIATES

(71) Applicant: BRACCO IMAGING SPA, Milan (IT)

(72) Inventors: Alessandro Barge, Turin (IT);
Francesca Baricco, Turin (IT);
Giancarlo Cravotto, Turin (IT);
Roberta Fretta, Collegno (IT);
Luciano Lattuada, Cassina de' Pecchi (IT)

(73) Assignee: BRACCO IMAGING SPA, Milan (IT)

( * ) Notice: Subject to any disclaimer, the term of this patent is extended or adjusted under 35 U.S.C. 154(b) by 0 days.

(21) Appl. No.: 16/466,104

(22) PCT Filed: Dec. 4, 2017

(86) PCT No.: PCT/EP2017/081373
§ 371 (c)(1),
(2) Date: Jun. 3, 2019

(87) PCT Pub. No.: WO2018/104228
PCT Pub. Date: Jun. 14, 2018

(65) Prior Publication Data
US 2020/0079728 A1    Mar. 12, 2020

(30) Foreign Application Priority Data
Dec. 5, 2016 (EP) ..................................... 16202152

(51) Int. Cl.
*C07C 231/02* (2006.01)
*C07C 231/12* (2006.01)

(52) U.S. Cl.
CPC .......... *C07C 231/02* (2013.01); *C07C 231/12* (2013.01); *C07C 2601/16* (2017.05)

(58) Field of Classification Search
None
See application file for complete search history.

(56) References Cited

U.S. PATENT DOCUMENTS 4,001,323 A * 1/1977 Felder ................ A61K 49/0433
564/153
4,352,788 A   10/1982 Felder et al.
5,043,152 A    8/1991 Schaefer et al.
(Continued)

FOREIGN PATENT DOCUMENTS

EP      0026281 A1    4/1981
EP      0083964A1 A1  7/1983
(Continued)

OTHER PUBLICATIONS

Merck Index Entry for Acetaminophen, downloaded from https://www.rsc.org/Merck-Index/monograph/m1317/acetaminophen?q=authorize on Feb. 25, 2020 (Year: 2020).*
(Continued)

*Primary Examiner* — Amy C Bonaparte
(74) *Attorney, Agent, or Firm* — Vivicar Law, PLLC

(57) ABSTRACT

The present invention generally relates to a process using a mechanochemical approach exploiting the mechanical milling of reactants for the manufacturing of acetyl Iopamidol and, more generally, of key intermediates of radiographic contrast agents, and of the contrast agents themselves.

16 Claims, 4 Drawing Sheets

(56) References Cited

U.S. PATENT DOCUMENTS

| | | | |
|---|---|---|---|
| 5,075,502 A | | 12/1991 | Kneller et al. |
| 5,965,772 A | * | 10/1999 | Desantis ............... C07C 231/08 564/153 |
| 6,350,908 B1 | * | 2/2002 | Desantis ............... C07C 231/02 564/142 |
| 9,006,488 B1 | * | 4/2015 | Amin ................... C07C 231/02 564/134 |

FOREIGN PATENT DOCUMENTS

| | | |
|---|---|---|
| GB | 1472050 A | 4/1977 |
| WO | 1994014478 A1 | 7/1994 |
| WO | 1996037459 A1 | 11/1996 |
| WO | 1996037460 A1 | 11/1996 |
| WO | 9709300 A1 | 3/1997 |
| WO | 1997047590 A2 | 12/1997 |
| WO | 1998024757 A1 | 6/1998 |
| WO | 1998028259 A1 | 7/1998 |
| WO | 1998054124 A1 | 12/1998 |
| WO | 1999058494 A2 | 11/1999 |
| WO | 2000015602 A1 | 3/2000 |
| WO | 2009103666 A2 | 8/2009 |
| WO | 2010057765 A1 | 5/2010 |

OTHER PUBLICATIONS

Sigma Alrich specification sheet for 98% Acetyl Chloride (reagent quality), downloaded from https://www.sigmaaldrich.com/Graphics/COfAInfo/SigmaSAPQM/SPEC/32/320129/320129-BULK_ALDRICH_.pdf on Feb. 28, 2020 (Year: 2020).*

Sigma Aldrich Specification sheet for 98% Acetic Anhydride (reagent quality), downloaded from https://www.sigmaaldrich.com/Graphics/COfAInfo/SigmaSAPQM/SPEC/24/242845/242845-BULK_SIAL_.pdf on Feb. 28, 2020 (Year: 2020).*

Sigma Aldrich specification sheet for 98% Serinol, downloaded from https://www.sigmaaldrich.com/catalog/DataSheetPage.do?brandKey=ALDRICH&symbol=357898 on Feb. 28, 2020 (Year: 2020).*

Green, T.W. and Wuts, P.G.M. (eds.), "Protection for the Amino Group," In: Protective Groups in Organic Synthesis, John Wiley & Sons, Inc., N.Y. (1999).

PCT Search Report and Written Opinion for PCT/EP2017/081373, dated Feb. 8, 2018.

The Merck Index, XIII ed., p. 5077, No. 5073 "Iopamidol," (2001).

* cited by examiner

RETCH™
SOLUTIONS IN MILLING & SIEVING

PM100 JAR 50 mL a)

b)

MECHANOCHEMICAL SYNTHESIS OF RADIOGRAPHIC AGENTS INTERMEDIATES

CROSS-REFERENCE TO RELATED APPLICATIONS

This application is the national stage application of corresponding international application number PCT/EP2017/081373, filed Dec. 4, 2017, which claims priority to and the benefit of European application no. 16202152.1, filed Dec. 5, 2016, all of which are hereby incorporated by reference in their entirety.

FIELD OF THE INVENTION

The present invention relates to the preparation of radiographic contrast agents. In particular it relates to the application of the mechanochemistry to the preparation of key intermediates of x-ray contrast agents, and to a general procedure for the preparation of the contrast agents themselves.

STATE OF THE ART

Iodinated contrast agents are well-known compounds widely used in x-ray imaging diagnostic techniques. Suitable examples of the said compounds and their precursors are, for instance, provided in WO2009/103666 (Bracco) and in the cited literature. Additional examples of similar iodinated contrast agents are also described, for instance, in WO 94/14478 (Bracco).

As an example, Iopamidol (The Merck Index, XIII Ed., 2001, No. 5073) S—(N,N'-Bis[2-hydroxy-1-(hydroxymethyl)ethyl]-5-[[(2S)-2-hydroxy-1-oxopropyl]-amino]-2,4,6-triiodo-1,3-benzenedicarboxamide, a well-known radiographic contrast agent widely used in daily diagnostic practice, can be prepared by using a synthetic procedure disclosed e.g. in GB1472050.

Another process for Iopamidol synthesis starts from the dichloride of the 5-amino-2,4,6-triiodoisophtalic acid (I) and may be schematically represented by the following Scheme 1

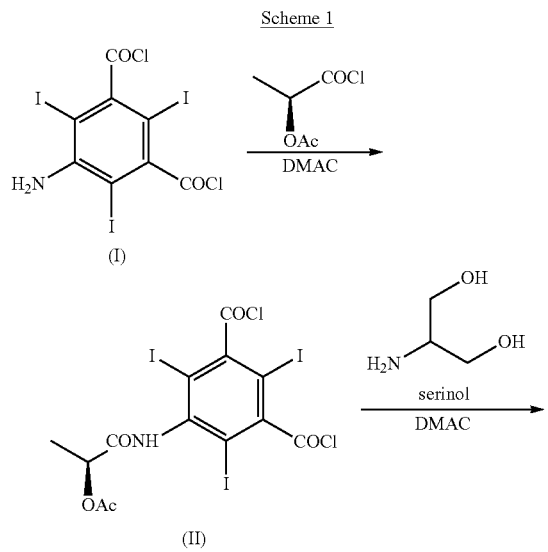

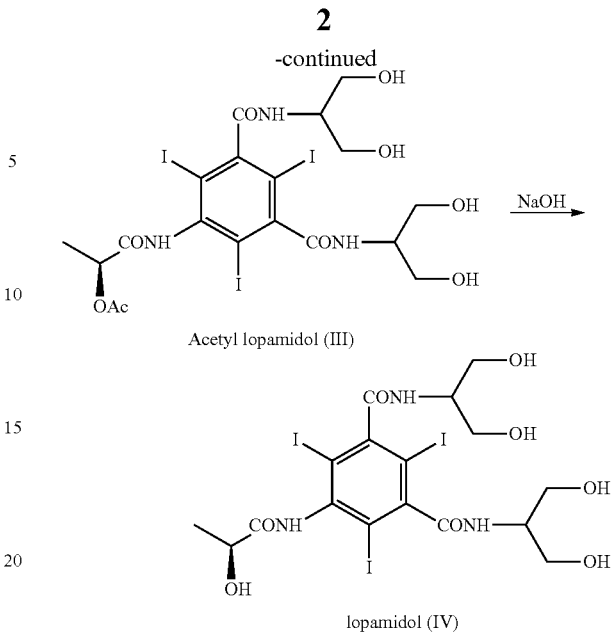

in which:
(I) is converted into the corresponding compound of formula (II) in the presence of (S)-2-acetyloxypropionyl chloride; and
the intermediate compound of formula (II) is converted into the Acetyl-Iopamidol of formula (III) in the presence of 2-amino-1,3-propandiol (serinol).

Then, the hydrolysis of the compound of formula (III) and the subsequent purification of the obtained product allow to isolate Iopamidol, the radiographic agent of the above formula (IV). Steps of the above process and their alternative are disclosed for instance in: WO96/037459, WO96/037460, WO97/047590, WO98/24757, WO98/028259 and WO99/58494.

In the industrial process currently used, the preparation of the intermediate compound (III) is commonly carried out in N,N-dimethylacetamide (DMAC) as a reaction solvent. The work up of the reaction step converting the obtained intermediate in the desired radiographic agent comprises evaporating under vacuum the reaction solvent to an oily residue that is diluted with water, purified over ion-exchanging resins, and then hydrolyzed to Iopamidol with NaOH.

As DMAC is a high boiling solvent (165° C.), its distillation may be a rather troublesome operation, especially with processes carried out on industrial scale.

WO00/15602 discloses a process for the preparation of Iopamidol where the intermediate (III) is obtained by reacting the intermediate (II) with a large excess (from 6 to 25 times) of serinol under heating.

The use of a suitable base, e.g. a tertiary amine or an alkaline metal or alkaline earth metal oxide or hydroxide, neutralizing the acid formed in the coupling reaction of compound (II) with 2-amino-1,3-propandiol carried out in DMAC is disclosed, respectively, e.g. in WO98/24757 and in WO2010/057765.

SUMMARY OF THE INVENTION

The present invention generally relates to the use of a mechanochemical approach exploiting the mechanical milling of reactants for the manufacturing of acetyl Iopamidol and, more generally, of key intermediates of radiographic contrast agents, and of the contrast agents themselves.

In particular, in one aspect the present invention relates to a new process for manufacturing Acetyl Iopamidol by amidation of the substrate compound of formula (II) with serinol, according to the following Scheme 2

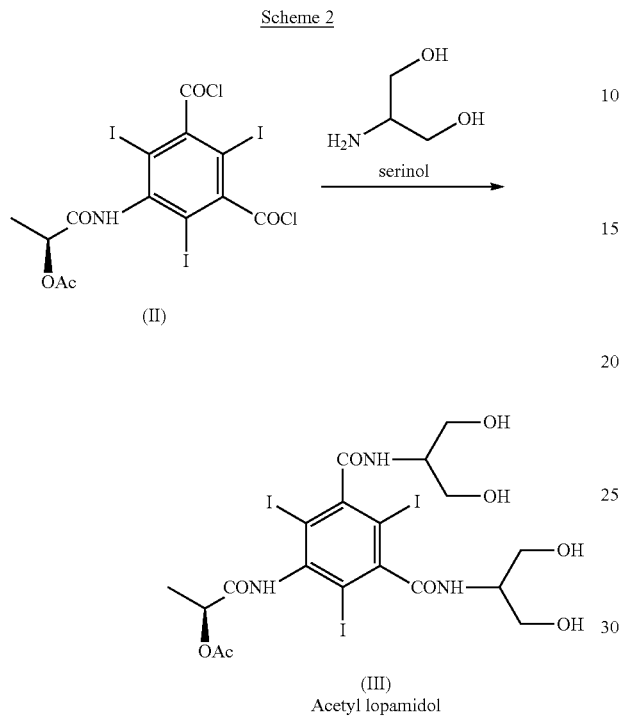

in which the amidation reaction is carried out by mechanical milling of compound (II) and serinol.

In another aspect the invention relates to a new process for the preparation of Iopamidol which comprises obtaining Acetyl Iopamidol by mechanical milling of compound (II) and serinol according to the synthetic approach provided by the present invention, and then converting the radiographic intermediate into the final radiographic agent (Iopamidol).

More particularly, in a further aspect the invention relates to a new process for the synthetic preparation of Iopamidol which comprises:
 a) obtaining Acetyl Iopamidol by mechanical milling of compound (II) and serinol; and, without isolation
 b) converting the obtained intermediate into Iopamidol, e.g. under basic conditions, promoting the removal of the acetyl group.

Interestingly, the solution identified by the present invention, that comprises exploiting the mechanical milling of reactants for manufacturing Acetyl Iopamidol is of general applicability, and provides a synthetic route generally exploitable for the preparation of key intermediates of radiographic contrast agents.

In particular, the above reaction is carried out by using a reduced excess of serinol, (e.g. below 6 times the substrate (II) amount) and without providing any external heating to the reacting mixture.

Intermediates that may conveniently be prepared by using the mechanochemical approach proposed by the present invention include iodinated compounds of formula (V)

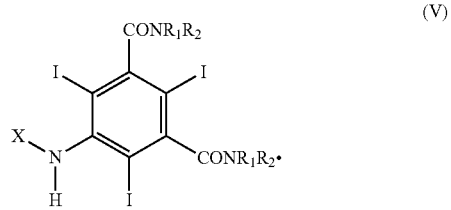

in which:
 $R_1$ is a $C_1$-$C_6$ alkyl substituted by one or more hydroxyl groups;
 $R_2$ is H or a $C_1$-$C_6$ alkyl optionally substituted by one or more hydroxyl groups; and
 X is selected from the groups consisting of: H, Pg, and —$COR_3$, where
  $R_3$ is a $C_1$-$C_6$ alkyl, optionally substituted by one or more $C_1$-$C_4$ alkoxy or acetyloxy (—OAc) groups, and
  Pg is an amino protecting group.

In an additional embodiment, therefore, the invention relates to a process for the synthetic preparation of a radiographic intermediate of the above formula (V)

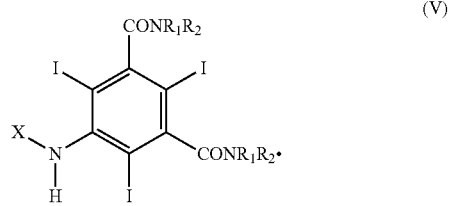

where X, $R_1$ and $R_2$ are as above said, which comprises:
 a) obtaining a 5-amino-2,4,6-triiodo-1,3-benzendicarboxylic acid dichloride of formula (VI) in which X is as defined for compounds of formula (V);

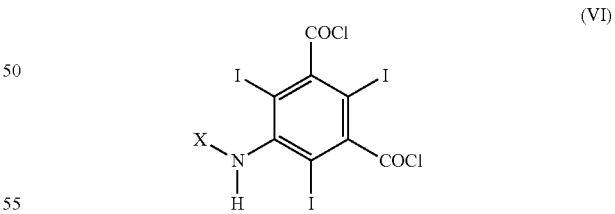

and
 b) reacting the obtained dichloride with an amine of formula $NHR_1R_2$;
in which the reaction of step b) is carried out by mechanical milling of reactants, according to the solution identified by the present invention.

In a still further aspect the invention relates to a general process for the preparation of a radiographic contrast agent of formula

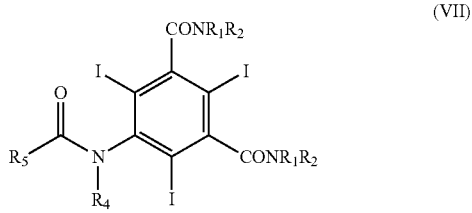

(VII)

in which:
R$_1$ and R$_2$ are as above defined for compounds of formula (V),
R$_4$ is H, or a C$_1$-C$_5$ alkyl optionally substituted by one or more groups independently selected from hydroxyl (—OH) and C$_1$-C$_3$ alkoxy;
R$_5$ is a C$_1$-C$_6$ alkyl, optionally substituted by one or more hydroxyls or C$_1$-C$_4$ alkoxy groups, which comprises obtaining an intermediate compound of formula (V) by mechanical milling of reactants, according to the process of the present invention, and then converting it into the final radiographic agents, e.g. by means of procedures known in the art.

DETAILED DESCRIPTION OF THE INVENTION

Figure 1A:
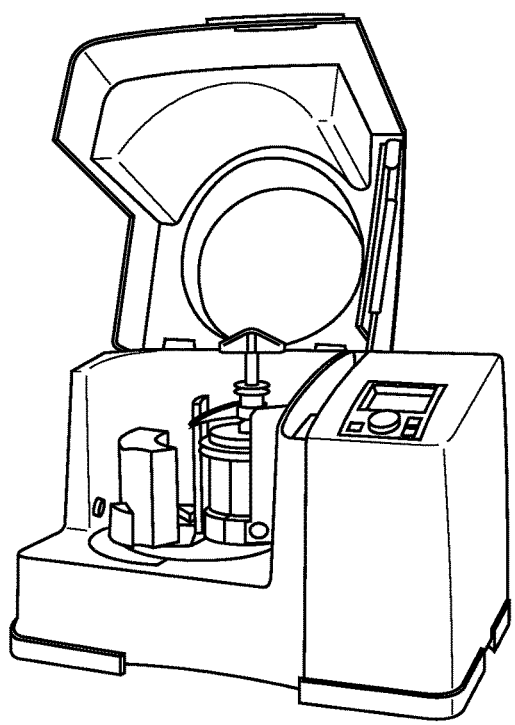
FIG. 1: Commercial planetary mill. Panel a) Planetary Ball Mill PM100; panel b) grinding jars; panel c) grinding balls (inside the jar).

The present invention relates to a process for the preparation of Acetyl Iopamidol and, more generally, of key intermediated of x-ray contrast agents and the contrast agents themselves by mechanical milling of the reactants.

Mechanical milling, as disclosed herein, is suitable for effectively exploiting the desired chemical reaction based on the principles of mechanochemical chemistry (or mechanochemistry), whereby mechanical forces transmit to a chemical system the energy required to activate a given reaction (IUPAC definition of mechanochemistry: "a chemical reaction that is induced by the direct absorption of mechanical energy")

In particular, an object of the present invention is a process for the preparation of Acetyl Iopamidol in which this compound is obtained by mechanical milling of compound (II) and serinol. In an embodiment, the mixture undergoing mechanical milling essentially consists of compound (II) and serinol.

The wording "milling" or "mechanical milling" as used herein comprises within its meaning a process carried out in a ball mill system, commonly a milling jar charged with steel balls, e.g. a Planetary ball Mill or a Horizontal Ball Mill, where the necessary mechanical energy for grinding and mixing (of the reactants), and to climb the activation barrier (of the chemical reaction) is generated by high-energy collisions from the milling balls and friction with inner wall of the jar.

To this extent, it is clear to a skilled person that "mechanical milling" of reactants, and, specifically, of compound (II) and serinol according to the process of the invention, includes the simultaneous milling of compound (II) and serinol that are comprised together in the milling jar, thereby leading to the formation of Acetyl Iopamidol as the reaction product of the mechanical "co-milling" or "milling", herein used interchangeably.

In the process of the invention the mechanical milling of reactants is carried out in a grinding equipment, for instance a planetary ball mill or a horizontal ball mill as said, equipped with a milling jar in which the proper amounts of the reactants are loaded together with stainless steel balls.

Non-limiting examples of appropriate mills already on the market are provided in FIG. 1-4.

Proper amounts of compound (II) and serinol are loaded in the jar (of the ball milling equipment), preferably at room temperature.

Because of the stoichiometry of the involved reaction, the molar ratio between the substrate compound undergoing amidation, e.g. compound (II), and the amine, e.g. serinol, is of at least 2.

Accordingly, in the process of the instant invention at least 2 moles of serinol will be loaded in the milling jar for each mole of loaded compound (II). An excess of serinol is however preferred, preferably of less than 6 moles of serinol for each mole of the dichloride (II), enabling both the coupling (amidation) reaction and the neutralization of the produced hydrochloric acid.

In particular, in one embodiment (when only serinol and compound (II) are co-milled) the process of the invention is carried out by using a molar ratio of from 2 to less than 6 and, more preferably, from 3 to less than 6, even more preferably from 4 to 5.5, e.g. 5 moles of serinol for each mole of compound (II) loaded in the milling jar.

In a preferred embodiment, a base may further be added to the co-milled reactants; while contributing to the neutralization of the formed hydrochloric acid, it allows reducing the total amount of serinol.

In this case, the process of the invention may be carried out by using from 2 to 5, preferably from 2 to 4, more preferably from 2 to 3 moles of serinol for each mole of co-milled compound (II).

Examples of suitable bases include inorganic bases, for instance selected from CaO, and Na$_2$CO$_3$, and organic bases, e.g. including tertiary amines such as triethylamine, triethanolamine (TEA) and N-methylmorpholine, these last two being particularly preferred.

In one embodiment, the process of the invention is carried out by using at least two moles of an additional base for each mole of compound (II) undergoing amidation.

An excess of the base is however preferred. For instance, the process of the invention may be carried out by using from about 2.5 to about 12, preferably from 3 to 10, more preferably from 4 to 8, even more preferably from 4.5 to 7 moles of an additional base for each mole of the acid dichloride of formula (II) undergoing amidation reaction with serinol.

In one embodiment the process of the invention is carried out in the presence of an inorganic base, preferably of Na$_2$CO$_3$. More preferably the process is carried out by using a molar ratio compound (II):serinol:Na$_2$CO$_3$ of 1:2:5.

In one alternative embodiment the process of the invention is carried out in the presence of an organic base, e.g. a tertiary amine; in a preferred embodiment the organic base is a liquid amine.

The use of an additional liquid base, such as triethanolamine or N-methylmorpholine, in the above amounts is in general preferred for large scale productions.

Further to allowing a reduction of the excess of serinol, these liquid amines may in fact act as suitable lubricants, contributing to prevent the formation of possible sticky material inside the jar when working with greater amounts of reactant.

In a particularly preferred embodiment the invention thus relates to a process for the preparation of Acetyl Iopamidol by mechanical milling of a mixture comprising of compound (II), serinol and an organic base selected from triethanolamine and N-methylmorpholine. In one embodiment, said mixture essentially consists of compound (II), serinol and said organic base.

Most preferably the process of the invention is carried out by using from 2 to 5, preferably for 2 to 4, more preferably from 2 to 3 e.g., most preferably, about 2.5 moles of serinol, and from 2.5 to 12, preferably from 3 to 10, more preferably from 4 to 8, even more preferably from 4.5 to 7, e.g., most preferably, from 5 to 6 moles of an organic base selected from triethanolamine and N-methylmorpholine for each mole of substrate compound (II) under reaction.

In the practice, the Applicant observes that it is useful to add an amount, by volume, of the liquid base approximately corresponding to the amount, by weight, of the substrate compound (e.g. compound (II)) undergoing amidation, or a half of said amount, up to e.g. twice the same.

In practical terms, the proper amounts of compound (II), serinol and optional base are (co-)loaded in the jar (of the ball milling equipment), suitably equipped with stainless balls of appropriate number and dimension.

To this extent, the dimension of the jar, the number and dimension of the stainless steel balls are suitably selected based on the scale of the mechanochemical reaction. For instance, when preparing Acetyl Iopamidol on a laboratory scale, a milling jar of from 10 to 300, e.g. from 25 to 125 mL can conveniently be used, charged with appropriate stainless balls. For instance, smaller jars, for example of about 50 mL may be conveniently loaded with balls of diameter (Ø) less than 10 mm, for instance with at least 20, e.g. from 20 to 100 and, more preferably from 40 to 60 balls with a diameter of about 5 mm, or with more than 1000, e.g. from 1000 to 2000 and, preferably with about 1500 balls having a smaller diameter, for example of about 2 mm. Greater stainless steel ball, for instance with a diameter of at least 10 mm, and preferably, equal to or larger than 15 mm e.g. up to 25 mm diameter are instead preferably used with larger jars, when working with greater quantities of reactants. For instance, from 20 to 30 balls of about 10 mm diameter and from 40 to 70 balls of about 5 mm diameter may be jointly used with jars of 125 mL, while e.g. 10-15 balls of about 20 mm of diameter are preferably used together with e.g. 50-70 balls of about 5 mm of diameter when working with jars of about 250 mL. Balls of up to 40 mm diameter may otherwise be used with largest mills, when working on an industrial scale.

Preferably all reactants are directly loaded (namely co-loaded) in the jar at room temperature, e.g. at once, or, alternatively, portionwise.

After loading of reactants, the grinding balls inside the jar are subjected to rotational movements generating the high energy collisions (from the balls) promoting the very efficient grinding and mixing of reactants. For instance, in a planetary mill the jar describes a circular path whilst simultaneously spinning in the reverse direction, mimicking the motion of planets around the sun, thereby generating high-energy collisions between milling balls and friction with the inner wall of the jar. Spinning blades are otherwise used, e.g. in larger equipments, to move the grinding balls at the desired rotation speed.

The process of the invention is carried out by using a rotation speed of the milling equipment of least 200 rotations per minute (rpm); preferably of from 200 to 1500 rpm, more preferably from 400 to 1000, and most preferably of about 500 to 700, e.g. at about 650 rpm per minute. When larger equipments are used, e.g. including horizontal ball mills or even larger mills for industrial use, the process is suitably carried out by subjecting the mill system to a rotation frequency of at least 120 rpm, preferably of from 120 to 1000 rpm, more preferably from 230 to 650 and most preferably of from about 280 to 550 rpm.

Suitably jacketed equipments may be used, particularly for large scale productions, allowing to counteract unwanted or uncontrollable increase of the temperature inside the jar, generally promoted by the collisions during the milling process. The jacket is preferably cooled with water, preferably circulating water at a temperature of from 10 to 20° C., preferably of about 15° C.

The appropriate grinding time and, in turn, the optimal reaction time will be closely related to all the above parameters. In particular, longer reaction times will be required for reaction carried out in larger equipment, or less powerful mill, having a reduced or suboptimal rotation speed, allowing less energy (and, hence, less effective) collisions.

For instance, when working with an equipment having high rotation speed, higher than 400 rpm, e.g. preferably around 650 rpm, an almost exhaustive amidation of the compound (II) is obtained in less than 3 hours, for instance in a time ranging from 20 to 180 min, and, preferably, from 20 to 120, more preferably, from 30 to 90 and, most preferably, from about 30 to about 60 min.

Longer times are instead preferred when the process is carried out at lower rotation speeds (of the milling jar), or with larger equipment, e.g. when working on an industrial scale. For instance, reaction times greater than 50 min, and preferably of from 50 to 180 min, more preferably from 50 to 120 min are preferred when the grinding process is carried out at reduced power/rotation speed (e.g. 400 rpm), or with large amounts of reactants.

Advantageously, however, even when working with larger equipments, the process of the invention leads to the desired compound, e.g. Acetyl Iopamidol, in less than 3 hour.

Therefore, in one aspect the proposed process results in a significant reduction of the overall reaction time required by industrial processes currently in use. These last, in fact, besides requiring the slow addition of serinol to a cooled solution of compound (II) (to keep under control the reaction temperature), take about 8 hours to achieve a completion of the amidation reaction.

A particularly advantageous reduction of the reaction time is observed when comparing the time required to obtain Acetyl Iopamidol in the absence of any solvent by means of the process disclosed in WO00/15602, using a large excess of serinol, and by mechanical co-milling of (only) serinol and compound (II), according to the solution identified by the invention.

Indeed, as shown in Table 1 of the Experimental section, the times required to achieve a completion of the amidation reaction in the experimental tests 1-4 of WO00/15602 range from about 40 to about 70 h, whereas corresponding reaction times used in the experimental tests of examples 1-3 of the Experimental Section is well below 2 hours.

Moreover, an even further reduction (in the reaction time) is unexpectedly achieved when the mechanical co-milling of the serinol and compound (II) is carried out in the presence of a liquid base such as triethanolamine or N-methylmorpholine. In this case, in fact, a completion of the amidation reaction is advantageously obtained in a very short time, e.g. of about one hour or even less, for example of about 30 minutes, as for instance verified with experimental tests of Examples 7 and 8 of the experimental section.

On the other side, the mechanical milling of reactants (exploited in the new process of the invention) is able to promote a very efficient mixing of the same making possible to obtain the desired product (e.g. Acetyl Iopamidol) by simply mixing the two solid reactants, optionally in combination with small amounts of a (liquid) base.

In an alternative embodiment a small amount of a liquid lubricant may optionally be added, e.g. when working on an industrial scale, for further preventing the formation of any optional "glue effect" slowing or hampering high energy collision from the balls.

Suitable liquid lubricants include for instance dipolar solvents such as DMAC, DiGlyme, N-methyl-2-pyrrolidone, Dimethylsulfoxyde (DMSO), Acetonitrile ($CH_3CN$), N,N-Dimethyloctanamide, N,N-Dimethyldecanamide and Diethylene glycol diethyl ether. Preferred are DMAC, DMSO and DyGlyme that act as useful lubricant and further contribute to at least partially dissolve the reactants, and $CH_3CN$ acting only as a lubricant. Particularly preferred are DMAC, DMSO and $CH_3CN$.

In one embodiment the process of the invention is carried out by using an amount of a lubricant, e.g. ranging, by volume, from about 0.5 to 1.5 times the amount, by weight, of compound (II) subjected to the amidation reaction. Preferably, the amount (by volume) of lubricant added in the milling jar corresponds to the amount by weight of the charged compound (II) and, more preferably, to the half of its weight.

Although very small, the above amount of lubricant is sufficient to prevent the formation of any optional glue or gum, even when working with large quantities of reagents, e.g. on an industrial scale.

At the same time, advantageously, a so reduced volume of lubricant (optionally used in the process of the invention) makes unnecessary its elimination from the crude reaction. In fact, the dilution with water of the crude reaction allows to collect an aqueous solution of Acetyl Iopamidol that may be used as such, without isolation of the intermediate in the subsequent steps converting it to the final contrast agent, namely Iopamidol, for instance carried out through known procedures.

Water immiscible lubricants like N,N-dimethyloctanamide and N,N-dimethyldecanamide may otherwise be eliminated from the crude reaction by separation of the immiscible organic phase from the aqueous phase (collected from the jar) comprising the crude intermediate.

From all the foregoing it should be clear to a skilled practitioner that the process of the instant invention, essentially, comprises: i) loading compound (II) and serinol and the optional base and/or lubricant in a stainless steel jar suitably filled with appropriate balls; ii) carrying out the grinding process at the selected rotation speed, for an appropriate time.

According to a practical implementation, the proper amount of the compound (II), serinol and optional base and lubricant are loaded in the milling jar at room temperature, e.g. by addition of all the reagents (e.g. at once) in the jar loaded with steel balls.

Alternatively, the jar is first loaded with the optional lubricant, and then with the proper amounts of remaining reagents. After loading the jar is closed and inserted in the mill. The grinding process is then started, at rotation speed and for a time depending on the process scale (and, hence the dimension of the jar), the power of the equipment, the presence of additional base/solvent.

For example, according to one preferred implementation, solid compound (II) and serinol in a molar ratio e.g. ranging from 1:4 to 1:5.5 are loaded in a jar of about 50 mL, charged with stainless steel balls of diameter=5 mm (50 balls) and diameter=2 mm (1500 balls) and the solid mixture is then subjected to grinding at 650 rpm, for a time preferably of from 30 to 90, more preferably of from 30 to 60 min, sufficient to achieve the completion of the amidation reaction.

Alternatively, the jar equipped with steel balls is loaded with solid compound (II), serinol and an inorganic base such as $Na_2CO_3$ (about 2 moles of serinol, and about 5 mole of $Na_2CO_3$ for each mole of charged compound (II)), and then subjected to 650 rpm for a time of from 40 to 90 and most preferably from 50 to 70 min.

Larger mills, e.g. horizontal mills (for instance shown in FIGS. 2-4) suitably equipped with steel balls of greater diameters, e.g. of from 15 to 20 mm are preferably used when operating on semi preparative, or industrial scales.

In this last case, a small amount of a lubricant, e.g. ranging from 0.5 to 1 times the amount (by weight) of compound (II) undergoing amidation may be first charged in the jar. Solid compound (II) is then charged in the jar, giving a mixture (with the lubricant) which is added with serinol and the optional base. The resulting mixture is then subjected to grinding for a time of from 30 to 180 min, depending on the milling power and the dimension of the jar, and, preferably of from 40 to 120 min. A rotation frequency (of the milling jar) of at least 120 rpm, preferably higher than 230, more preferably higher from 340 and up to 1000 rpm, e.g., most preferably, from 440 to 750 rpm may be used, allowing to achieve the completion of the reaction in times lower that 3 h and preferably, lower than 2 hours.

According to a particularly preferred implementation, the process of the invention is carried out in the absence of any reaction solvent or additional lubricant, by mechanical milling of compound (II) and serinol carried out in the presence of a base selected from triethanolamine and N-methylmorpholine. In practical terms, compound (II) and amount of triethanolamine (or N-methylmorpholine) corresponding (by volume) to the amount (by weight) of the compound (II), or to its half, are charged in the jar and added with from 2 to 3, e.g. about 2.5 mole of serinol for each mole of the charged compound (II). The obtained mixture is then subjected to mechanical milling for a time of from 0.5 to 3 h, preferably of less than 2 hours, and more preferably of about 1 hour.

By using the above conditions, Acetyl Iopamidol is obtained with good yield and purity in a time lower than three hours, even when working with large quantities of reagents.

The process of the invention allows to obtain the desired compound with good yield and purity, fulfilling the analytical specifications for the industrially produced intermediate, that may thus be used as such in the subsequent conversion to the desired radiographic agent, typically without any isolation or additional purification.

A further object of the present invention therefore is a process for the preparation of (N,N'-Bis[2-hydroxy-1-(hydroxymethyl)ethyl]-5-[[(2S)-2-hydroxy-1-oxopropyl]- amino]-2,4,6-triiodo-1,3-benzenedicarboxamide, (namely Iopamidol) that comprises obtaining N,N'-Bis[2-hydroxy-1-(hydroxymethyl)ethyl]-5-[[(2S)-2-acetyloxy)-1-oxopropyl]-amino]-2,4,6-triiodo-1,3-benzenedicarboxamide (namely Acetyl Iopamidol) by mechanical milling of compound (II) and serinol, substantially as formerly disclosed.

More particularly, in a further aspect the invention relates to a process for the synthetic preparation of Iopamidol that comprises:

a) obtaining Acetyl Iopamidol by mechanical milling of compound (II) and serinol by use of the process of the invention; and, without isolation b) converting the obtained Acetyl Iopamidol into Iopamidol by hydrolysis of the acetyl group and purification of the crude compound.

The step a) of this process is carried out by means of the process of the instant invention, as extensively reported in the previous sections.

The step b) of the process, comprising converting the Acetyl Iopamidol resulting from the step a) into the final radiographic contrast agent (Iopamidol) may be carried out according to conventional methods, for instance reported in the relevant art.

For instance, the crude product recovered from step a) may be cooled to room temperature and then hydrolyzed to Iopamidol directly in the milling jar.

In particular, according to one embodiment, a proper amount of aqueous NaOH 30% is added to the crude mixture cooled to room temperature directly in the milling jar, and this last is then subjected to rotation of about 400 rpm for few minutes, e.g. from 1 to 20 and preferably from 5 to 10 minutes. The crude Iopamidol is then collected from the jar with water, and purified over exchange-ions resins and then crystallized according to know procedures.

Alternatively, an aqueous solution of the crude intermediate is first collected from the jar by washing the tank and balls with water, which is optionally purified by elution of the aqueous solution over ionic exchange resins, e.g. cationic resins such as Dowex C350, Amberlyst 15 Wet and Diaion SK, fixing the unreacted serinol and the optional base, and then hydrolyzed under basic conditions, e.g. by addition of NaOH 30% leading to the cleavage of the acetyl group (of the acetyl Iopamidol) with formation of the desired radiographic agent.

In particular, according to one preferred embodiment the invention relates to a new process for the synthetic preparation of Iopamidol carried out without isolation of Acetyl Iopamidol according to the following synthetic Scheme 3

Scheme 3

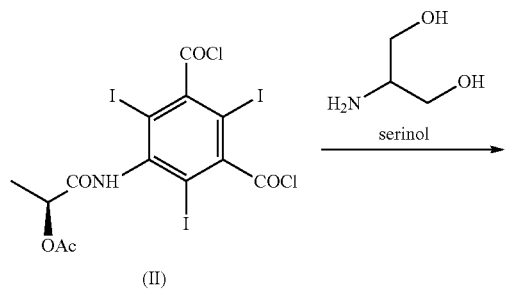

(II)

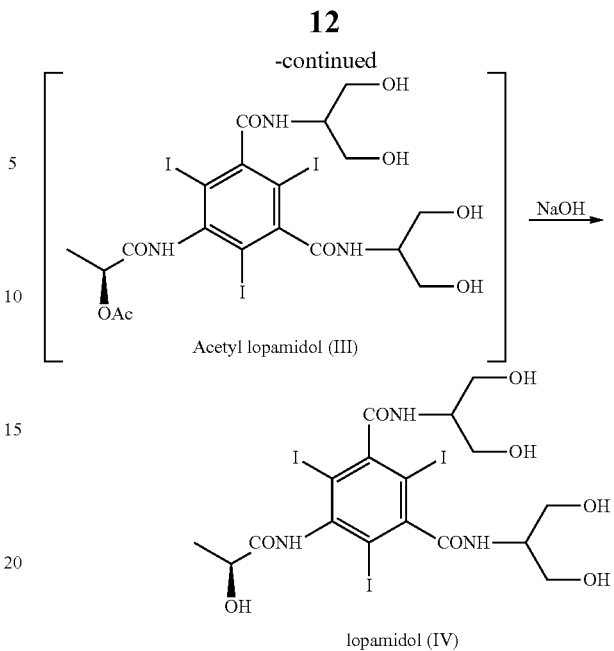

which comprises:

a) obtaining Acetyl Iopamidol by mechanical milling of compound (II) and serinol according to the process of the invention, as above discussed;

b) removal the crude Acetyl Iopamidol by the milling equipment, e.g. with water, and optional elution of the crude solution over exchange-ions resins;

c) hydrolysis of the acetyl group from collected Acetyl Iopamidol under basic conditions, typically with NaOH 30%, leading to Iopamidol;

d) purification over exchange-ions resins; and e) crystallization of Iopamidol.

Whilst the step a) of this process is carried out as above discussed, subsequent steps, comprehensive of experimental operative conditions and optional variants thereof are all to be performed according to conventional methods reported in the art.

For instance, the step c) of the process may conveniently be carried out by addition of NaOH 30% to the aqueous solution of Acetyl Iopamidol (collected from the milling jar or after elution over resins) up to a pH of about 10, for a time of about 7 h. The crude reaction may be then neutralized to a pH of 6-7 with HCl, and purified by ion exchange resins according to a conventional procedure, e.g. as disclosed in WO98/24757 and WO2010/057765, leading to an aqueous solution of Iopamidol that is then treated according to GB1472050 or as disclosed in WO97/09300.

By a comparison between reaction times and working-up conditions required by one industrial process to Iopamidol, e.g. broadly disclosed in WO98/24757, it clearly results that the process of the present invention for preparing Iopamidol, beside solving problems due to the use of high amounts of DMAC, requiring its elimination by evaporation of the crude reaction, further allows to reduce the overall reaction time, and the number of processing steps (of the crude reaction) leading to the isolation of the desired product.

In fact, while the industrial process requires a slow addition of a solution of serinol in DMAC to a cooled solution of compound (II) in DMAC in a time ranging from 5 to 20 h (to keep the reaction temperature <20° C.) and carrying on the reaction for up to 8 h before concentration of the crude reaction by evaporation of the DMAC, dilution with water, elution (of the aqueous solution of Acetyl Iopamidol) over cationic resin and conversion to Iopamidol by hydrolysis with NaOH, in the process of the invention all reactants are charged at once in the jar, e.g. at room temperature, and the completion of the amidation reaction (carried out by mechanical milling of reactants) is obtained in less than 3 hours, by leading to a crude mixture (comprising Acetyl Iopamidol) that does not requires any concentration or evaporation of the solvent, and that can be used as such after dilution with water in the next steps to Iopamidol.

As formerly discussed the approach exploited by the present invention, comprising carrying out the amidation of compound (II) with serinol by mechanical milling of reactants is of general applicability, and may more generally be exploited for the preparation of key intermediates of x-ray contrast agents.

Suitable examples of radiographic intermediates that may conveniently be prepared by using the mechanochemical approach of the present invention, i.e. by exploiting a mechanical milling of reactants, include iodinated compounds of the following formula (V)

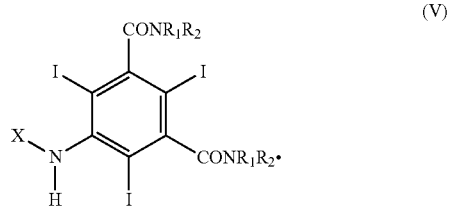

in which:
R$_1$ is a C$_1$-C$_6$ alkyl substituted by one or more hydroxyl groups;
R$_2$ is H, or a C$_1$-C$_6$ alkyl optionally substituted by one or more hydroxyl groups; and
X is selected from the groups consisting of: H, Pg, and —COR$_3$, where
R$_3$ is a C$_1$-C$_6$ alkyl, optionally substituted by one or more C$_1$-C$_4$ alkoxy or acetyloxy (—OAc) groups, and
Pg is an amino protecting group.

In the present description, unless otherwise indicated, the term "protecting group" includes in its meaning a group adapted to preserve the characteristic chemical function of the functional group to which it is bound. Specifically, in the present context, the protecting group Pg is used for preserving the function of the amino group to which it is bound. Suitable examples of appropriate amino protective groups include, for example, Carbobenzyloxy (Cbz), Benzoyl (Bz) and 9-Fluorenylmethyloxycarbonyl (FMOC) groups, wherein the first is preferred. [As a general reference to protecting groups, see T. W. Green and P. G. M. Wuts; Protective Groups in Organic Synthesis, Wiley, N.Y. 1999, third edition].

Unless otherwise provided, the expression "alkyl" comprises within its meanings any linear or branched hydrocarbon chain, preferably comprising up to 12 carbon atoms. In particular "C$_1$-C$_6$ alkyl" comprises within its meaning a linear or branched chain comprising from 1 to 6 carbon atoms such as: methyl, ethyl, propyl, iso-propyl, butyl, iso-butyl, tert-butyl, pentyl, iso-pentyl, tert-pentyl, hexyl, iso-hexyl, and the like.

Likewise, the term "alkoxy" comprises within its meanings any of the corresponding alkyl-oxy groups, including C$_1$-C$_4$ alkyloxy such as methoxy, ethoxy, n-propoxy, iso-propoxy and the like;

An additional object of the instant invention is a process for the preparation of a radiographic intermediate compound of the above formula (V) that comprises, as main steps:
a) obtaining a 5-amino-2,4,6-triiodo-1,3-benzendicarboxylic acid dichloride of formula (VI)

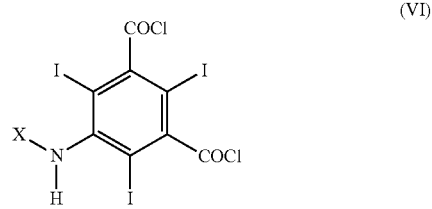

where X is as above defined for the compounds of formula (V), and
b) reacting the obtained dichloride with an amine of formula NHR$_1$R$_2$ where
R$_1$ and R$_2$ are as above defined, to give the corresponding diamide derivative, in which the amidation reaction of step b) of the process is carried out according to the scheme

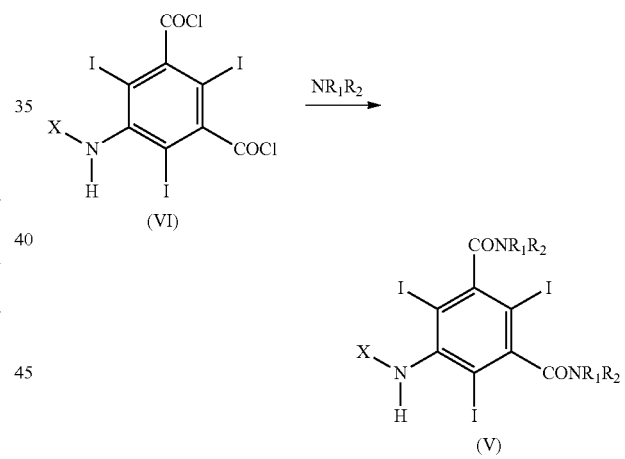

by mechanical milling of reactants, according to the solution identified by the present invention.

The step a) of the above process leading to the preparation of the dichloride of formula (VI) may, instead, be carried out according to well-known procedures, for instance disclosed in WO9637460, WO982828259 and U.S. Pat. No. 5,075,502.

Preferred according to the invention are intermediate compounds according to the above formula (V) in which:
R$_1$ is C$_1$-C$_3$ alkyl substituted by one or more and, preferably, two hydroxyl groups;
R$_2$ is H; and
X is H or —COR$_3$, where R$_3$ is a C$_1$-C$_3$ alkyl e.g. propyl, ethyl or methyl, optionally substituted by one or more groups selected from acetyloxy (—OAc) and methoxy (—OCH$_3$).

Particularly preferred are intermediate compounds selected from:

the compound of formula (VIII)

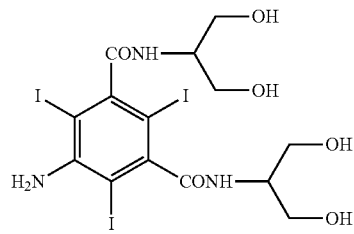

(VIII)

which is an alternative intermediate in the synthesis of Iopamidol, the compound of formula (IX)

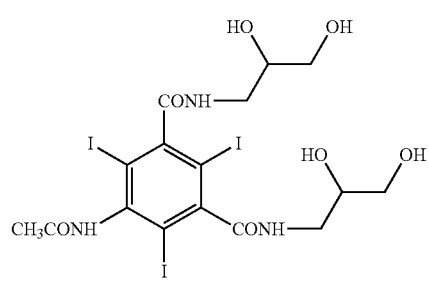

(IX)

which is a common intermediate in the synthesis of Iohexol®, Iopentol®, and Iodixanol®;

and the compound of formula (X)

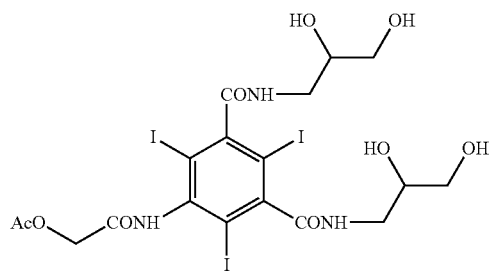

(X)

which is a useful intermediate in the preparation of both Iomeprol® and Ioversol®.

Once obtained, the intermediate compounds of formula (V) may be processed to the desired radiographic contrast agent according to procedure known in the art.

In a still further aspect the invention relates to a general process for the preparation of a radiographic contrast agent of formula (VII)

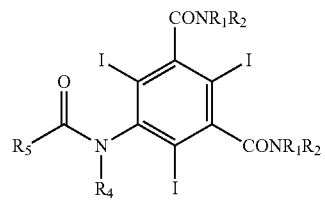

(VII)

in which:

$R_1$ and $R_2$ are as above defined for compounds of formula (V);

$R_4$ is H, or a $C_1$-$C_5$ alkyl optionally substituted by one or more groups independently selected from hydroxyl (—OH) and $C_1$-$C_3$ alkoxy;

$R_5$ is a $C_1$-$C_6$ alkyl, optionally substituted by one or more hydroxyls or $C_1$-$C_4$ alkoxy groups;

said process comprising starting from an intermediate compound of formula (V) obtained by mechanical milling of reactants, according to the solution identified by the present invention, and then converting it to the desired radiographic agent, e.g. according to conventional methods reported in the art, e.g. as disclosed in U.S. Pat. No. 5,043,152; EP0026281; and EP0083964.

Non limiting examples of radiographic contrast agents according to the above formula (X) that, the same as Iopamidol, may be obtained starting from a iodinated intermediate obtained by using the mechanical process of the present invention for instance include: Iomeprol, Iobitridol, Ioversol, Iopentol, Iohexol.

Further details concerning the process of the invention are reported in the following experimental section, with the sole aim to better illustrate the present invention, without representing any limitation to it.

EXPERIMENTAL SECTION

Characterization of the Obtained Compounds.

Acetyl Iopamidol

Yield and purity of the Acetyl Iopamidol recovered with the process of the invention has been determined by direct hydrolysis of the crude intermediate (Acetyl Iopamidol) and HPLC analysis of the obtained crude product (Iopamidol), by comparison with the pure compound as external standard.

General Procedure

HPLC Chromatographic Method

Stationary phase: Zorbax SB-Phenyl 80 Å 5 μm, 250×4.6 mm (Agilent Technologies)

Mobile phase: A: $H_2O$
B: $H_2O/CH_3CN$ 50/50 (v/v)

Elution: gradient elution gradient table:

| t (min) | phase A (%) | phase B (%) |
|---|---|---|
| 0 | 100 | 0 |
| 18 | 100 | 0 |
| 40 | 62 | 38 |
| 45 | 50 | 50 |
| 50 | 100 | 0 |
| 60 | 100 | 0 |

Temperature: 60° C.
Detection: UV (k=240 nm)
Flow: 2 mL min$^{-1}$
Sample concentration: 10 mg mL$^{-1}$
Injection: 20 μL
Iopamidol retention time: about 18 min
Compound VIII
Yield and purity of the intermediate compound VIII, recovered with the process of the invention has been determined by HPLC analysis of the crude reaction, by comparison with the pure compound as external standard.
Chromatographic Conditions
Stationary phase: Zorbax SB-Phenyl 80 Å 5 μm, 250×4.6 mm (Agilent Technologies)
Mobile phase: A: 0.0025 M KH$_2$PO$_4$ and 0.043 M H$_3$PO$_4$ in water
B: CH$_3$CN
Elution: gradient elution
gradient table:

| t (min) | phase A (%) | phase B (%) |
|---|---|---|
| 0 | 100 | 0 |
| 15 | 100 | 0 |
| 50 | 50 | 50 |

Figure 1B:
Figure 1C:
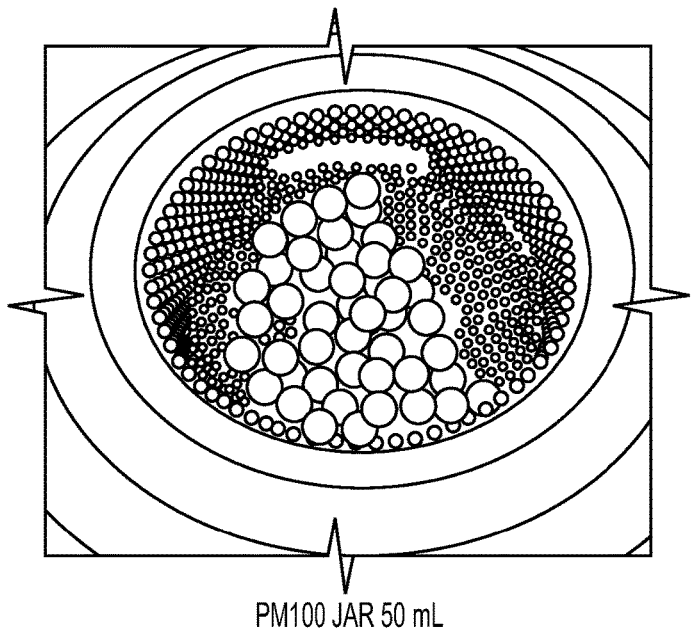
Figure 2:
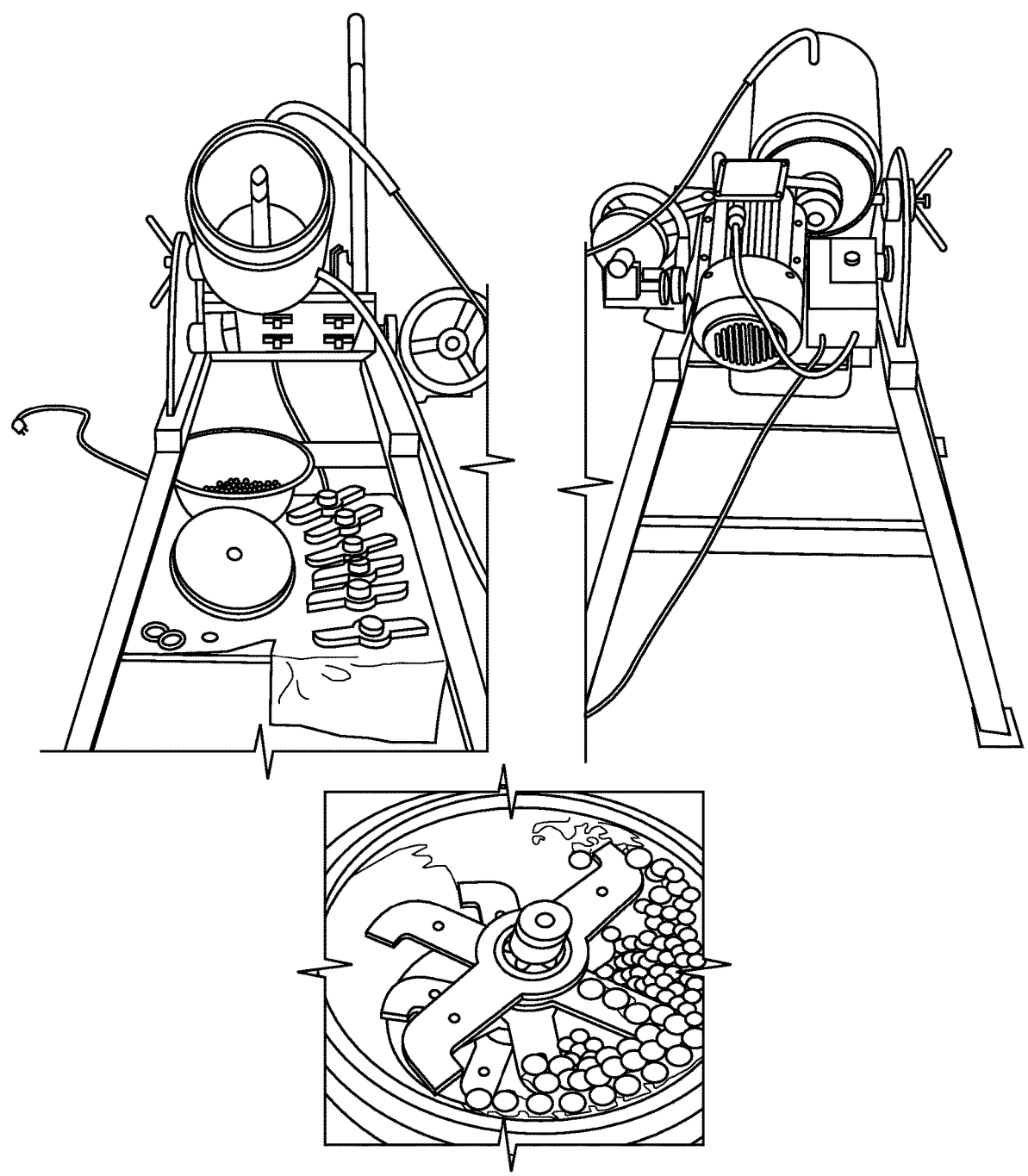
FIG. 2: Commercial example of Horizontal Rotary Ball Mill.
Figure 3:
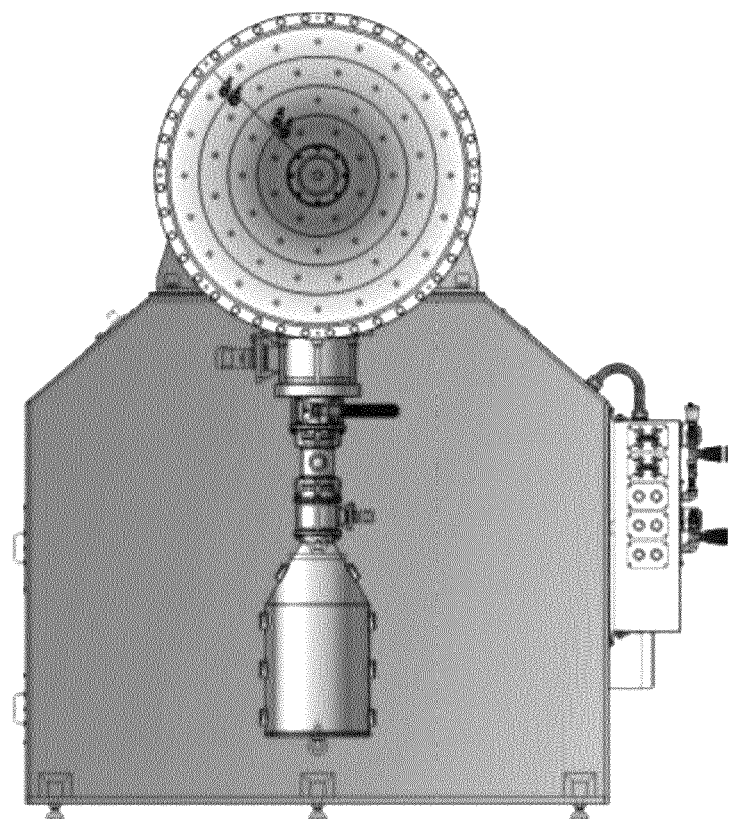
FIG. 3: Simoloyer® CM 900 for preparations on larger scale.
Figure 3:
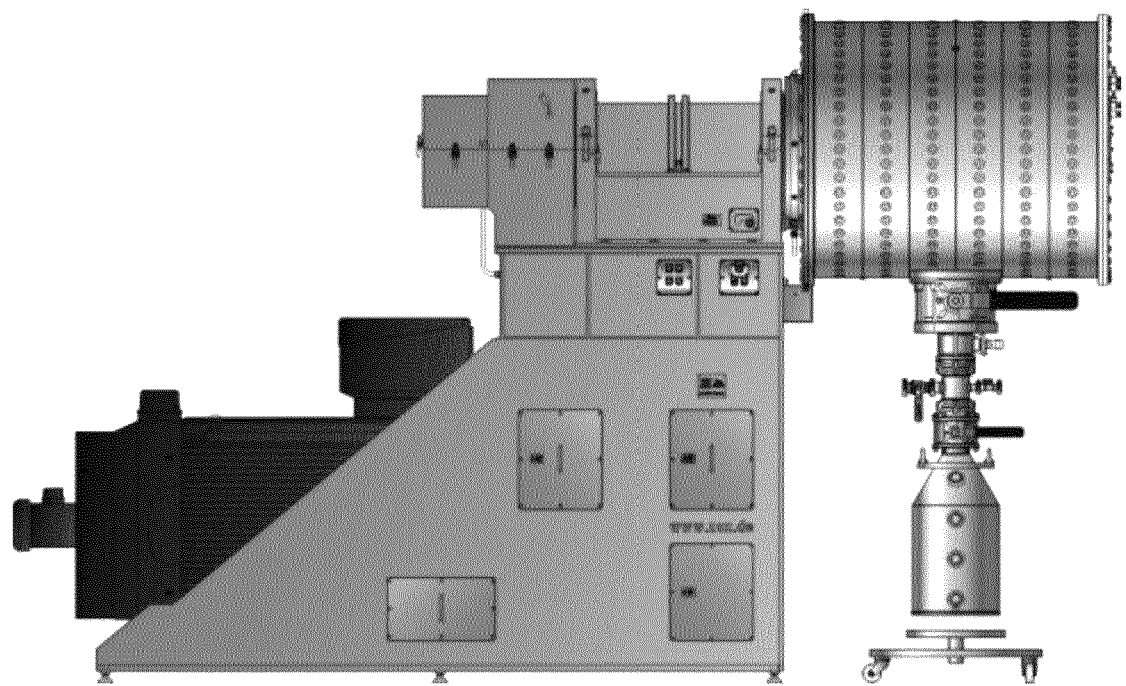
Figure 4:
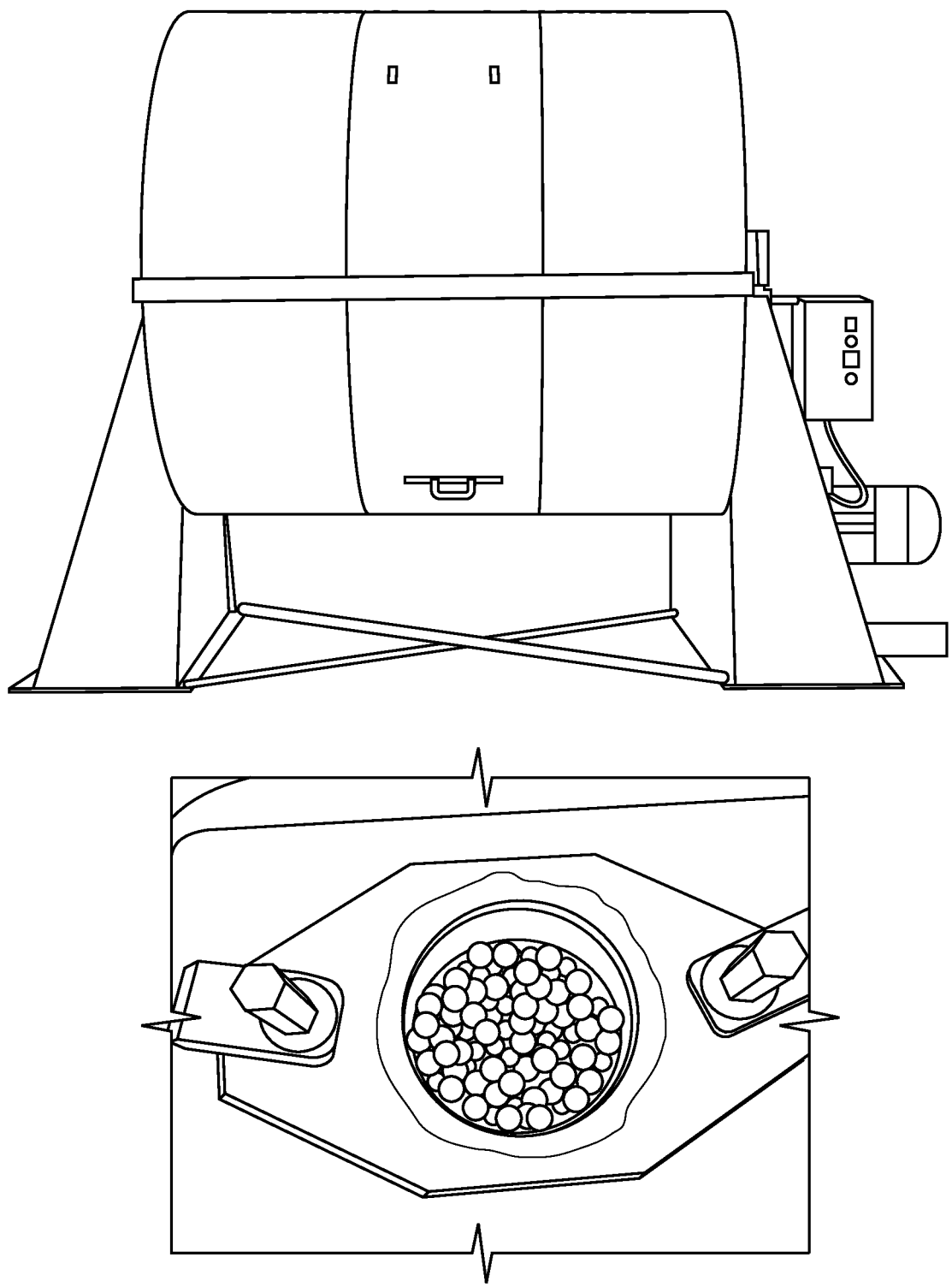
FIG. 4: Drum-Mill for preparations on industrial scale

Flow rate: 1.5 mL min$^{-1}$
Detection (UV): 240 nm
Injection: 20 μL
Sample concentration: 1 mg mL$^{-1}$ in water/acetonitrile 92:8
Temperature: 70° C.
Compound (VIII) retention time: about 16 min
Materials and Equipment
All commercially available reagents and solvents were used without further purification.
Mechanochemical reactions were performed in planetary ball mill PM100 (Retsch GmbH) (FIG. 1). The stainless steel milling jar (50 mL) was charged with two types of stainless steel balls: diameter=5 mm (50 balls) and diameter=2 mm (1500 balls).
Scale-up process was tested in a jacketed horizontal ball mill (FIG. 2). The milling tank (5 L) was charged with stainless steel ball with diameter=15 mm (350 balls)
Synthesis of Acetyl Iopamidol (General Procedure).
Stainless steel jar is filled with appropriate balls.
Solid compound (II), serinol (variable amount, depending on the selected molar ratio) and optional bases or solvent are added into the jar. The jar is closed and inserted in the ball mill.
The milling process is carried out at different rpm values varying the reaction time. Once obtained, the crude acetyl Iopamidol is not isolated but, as in the current industrial process, it is immediately converted to Iopamidol by hydrolysis. Yield and purity of the collected intermediate are then assessed by HPLC, based on the yield and purity of the Iopamidol in the crude (hydrolysis) reaction, measured by means of an external standard.
Hydrolysis of Acetyl Iopamidol to Iopamidol (General Procedure).
Hydrolysis Procedures:
a) After cooling of the crude reaction (obtained by mechanical milling of compound (II) and serinol) to room temperature, 30% NaOH (about 1 mL) is added directly in the jar, that is then subjected to 400 rpm for 10 min. The crude reaction is collected by washing the jar and balls with water.
The obtained solution was neutralized with 2 N HCl and the yield and purity of the obtained Iopamidol were determined by HPLC of the crude solution, by use of an external standard.
b) After cooling of the crude reaction to room temperature, the jar and balls are washed with water and the solution quantitatively recovered. The collected solution may be then directly added with 30% NaOH up to pH 10, and maintained under stirring overnight. Preferably, the obtained aqueous solution of Acetyl Iopamidol is first eluted over ion-exchange resins, typically a cationic resin such as Dowex C350, fixing optional serinol and bases in excess, for instance by using a ratio between resin and worked Compound (II) of about 3:1 (w/w), and then added with 30% NaOH up to pH 10 and maintained under stirring for 7 hours. The basic solution is then neutralized with 2N HCl. Yield and purity of the derived Iopamidol are determined by HPLC analysis of the crude solution, by use of an external standard.

Example 1

Preparation of Acetyl Iopamidol by Mechanical Milling of Compound (II) and Serinol
Reaction time 20 min; 650 rpm, molar ratio compound (II):serinol=1:5. Compound (II) (1 g, 1.40 mmol) and serinol (0.640 g; 7 mmol) are loaded in the jar filled with stainless steel balls of Ø=5 mm (50 balls) and Ø=2 mm (1500 balls). The jar is then closed, inserted in the mill and subjected to a 650 rpm for 20 min. After cooling to room temperature, the crude reaction is added with 30% NaOH (about 1 mL) and treated at 400 rpm for 10 min. The reaction mixture is collected from the jar with water and the obtained solution is neutralized with 2N HCl and analyzed by HPLC.
Yield: 82%

Example 2

Preparation of Acetyl Iopamidol by Mechanical Milling of Compound (II) and Serinol
Reaction time 40 min; 650 rpm; compound (II):serinol=1:5.
Compound (II) (1 g, 1.40 mmol) and serinol (0.640 g; 7 mmol) are loaded in the jar filled with appropriate stainless steel balls as in example 1. The jar is then closed, inserted in the mill and subjected to a 650 rpm for 40 min. After cooling to room temperature, the crude reaction is added with 30% NaOH (about 1 mL) and treated at 400 rpm for 10 min. The reaction mixture is collected from the jar with water and the obtained solution is neutralized with 2N HCl and analyzed by HPLC. Yield: 89%

Example 3

Preparation of Acetyl Iopamidol by Mechanical Milling of Compound (II) and Serinol
Reaction time 70 min; 400 rpm; compound (II):serinol=1:5.
Compound (II) (1 g; 1.40 mmol) and serinol (0.640 g; 7 mmol) are loaded in the jar filled with appropriate stainless steel balls as in example 1. The jar is then closed, inserted in the mill and subjected to a 400 rpm for 70 min. After cooling to room temperature, the crude reaction is added with 30% NaOH (about 1 mL) and treated at 400 rpm for 10 min. The reaction mixture is collected from the jar with water and the obtained solution is then neutralized with 2N HCl and analyzed by HPLC.
Yield: 61%

Example 4

Preparation of Acetyl Iopamidol by Mechanical Milling of Compound (II) and Serinol in the Presence of a Solid Base ($Na_2CO_3$)

Reaction time 30 min; 650 rpm; compound (II):serinol=1:2; compound (II):$Na_2CO_3$=1:5.

Compound (II) (1 g; 1.40 mmol), serinol (0.255 g; 2.8 mmol) and $Na_2CO_3$ (0.75 g; 7 mmol) are loaded in the jar filled with appropriate stainless steel balls as in example 1. The jar is then closed, inserted in the mill and subjected to a 650 rpm for 30 min. After cooling to room temperature, the crude reaction is added with 30% NaOH (about 1 mL) and treated at 400 rpm for 10 min. The reaction mixture is collected from the jar with water and the obtained solution is then neutralized with 2N HCl and analyzed by HPLC.

Yield: 73%

Example 5

Preparation of Acetyl Iopamidol by Mechanical Milling of Compound (II) and Serinol in the Presence of a Lubricant (DMAC)

Reaction time 55 min; 650 rpm, compound (II):serinol=1:5; compound (II) (w):lubricant (v)=1:1

Compound (II) (1 g, 1.40 mmol) and serinol (0.640 g; 7 mmol) and DMAC (1 mL) are loaded in the jar filled with appropriate stainless steel balls as in example 1. The jar is then closed, inserted in the mill and subjected to a 650 rpm for 55 min. After cooling to room temperature, the crude reaction is added with 30% NaOH (about 1 mL) and treated at 400 rpm for 10 min. The obtained mixture is collected from the jar with water and the solution is then neutralized with 2N HCl and analyzed by HPLC.

Yield: 99%

Example 6

Scale-Up of the Preparation of Acetyl Iopamidol by Mechanical Milling of Compound (II) and Serinol in the Presence of a Lubricant (DMAC)

(reaction time 3 h; rotation frequency 440 rpm, compound (II):serinol=1:5; compound (II) (w):solvent (v)=1:1

The reaction was tested in a horizontal ball mill in order to scale-up the procedure. The stainless steel tank (5 L) was charged with stainless steel ball with a diameter Ø=15 mm (350 balls), than solid compound (II) (300 g; 0.42 mol), serinol (192 g; 2.11 mol) and DMAC (300 mL) were added in the jar maintained in a vertical position during loading. The tank was closed and placed obliquely in the mill, so as to ensure a maximum efficiency of the balls inside the jar. The milling process was carried out at a rotation frequency of 440 rpm for 3 h. After cooling to room temperature the tank was washed with water and the solution quantitatively recovered. 30% NaOH (up to pH=10) was added to the solution which was stirred overnight. Then, it was neutralized with 2 N HCl and Iopamidol yield was determined by HPLC analysis by means of an external standard.

Yield: 97%.

Example 7

Preparation of Acetyl Iopamidol by Mechanical Milling of Compound (II) and Serinol in the Presence of a Liquid Base (Triethanolamine—TEA)

Reaction time 30 min; rotation frequency≈340 rpm, compound (II):serinol=1:2.5; compound (II) (w):TEA (v)=1:1

The reaction was tested in a horizontal ball mill. The stainless steel tank (5 L) was charged with stainless steel ball with a diameter=15 mm (350 balls), than solid compound (II) (100 g; 0.14 mol), serinol (32.4 g; 0.355 mol) and TEA (100 mL) were added in the jar. The tank was closed and placed obliquely in the mill. The milling process was carried out at a rotation frequency of 30 Hz 340 rpm for 30 min. After cooling to room temperature the tank was washed with water and the solution quantitatively recovered. 30% NaOH (up to pH=10) was added to the solution which was stirred overnight. Then, it was neutralized with 2 N HCl and Iopamidol yield was determined by HPLC analysis by means of an external standard.

Yield: 85%.

Example 8

Preparation of Acetyl Iopamidol by Mechanical Milling of Compound (II) and Serinol in the Presence of a Liquid Base (N-methylmorpholine)

Reaction time 30 min; 650 rpm; compound (II):serinol=1:5; compound (II) (w):N-methylmorpholine (v)=1:1

Compound (II) (1 g, 1.40 mmol) and serinol (0.640 g; 7 mmol) and N-methylmorpholine (1 mL) are loaded in the jar filled with appropriate stainless steel balls as in example 1. The jar is then closed, inserted in the mill and subjected to a 650 rpm for 30 min. After cooling to room temperature, the crude reaction is added with NaOH 30% (about 1 mL) and treated at 400 rpm for 10 min. The mixture is collected from the jar with water and the obtained solution is neutralized with HCl 2N and analyzed by HPLC.

Yield: 98%

Example 9

Preparation of Acetyl Iopamidol by Mechanical Milling of Compound (II) and Serinol in the Presence of a Liquid Base (N-methylmorpholine)

Reaction time 60 min; 650 rpm, compound (II):serinol=1: 2.5; compound (II) (w):N-methylmorpholine (v)=1:1

Compound (II) (1 g, 1.40 mmol) and serinol (0.320 g; 3.5 mmol) and N-methylmorpholine (1 mL) are loaded in the jar filled with appropriate stainless steel balls as in example 1. The jar is then closed, inserted in the mill and subjected to a 650 rpm for 60 min. After cooling to room temperature, the crude reaction is added with 30% NaOH (about 1 mL) and treated at 400 rpm for 10 min. The mixture is collected from the jar with water and the obtained solution is neutralized with 2N HCl and analyzed by HPLC.

Yield: 83%.

Example 10

Preparation of Intermediate (VIII) by Mechanical Milling of Reactants

The intermediate compound (VIII) was prepared by amidation of the substrate compound (I) with serinol, according to the following Scheme 4

Scheme 4

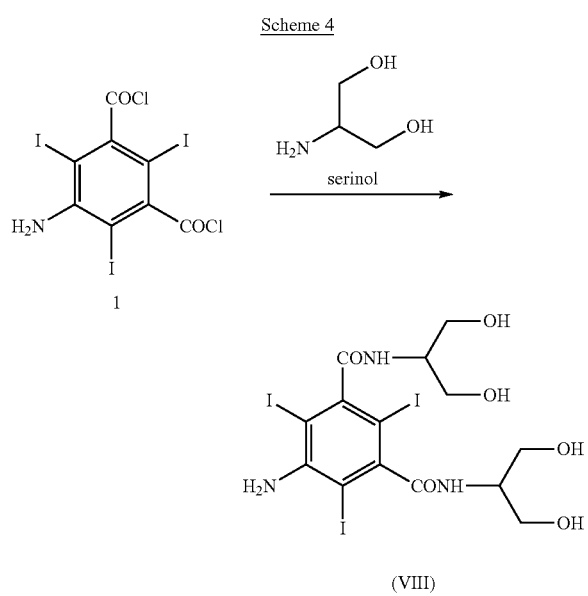

The amidation reaction was carried out in planetary ball mill PM100 (Retsch GmbH) equipped with stainless steel ball as in example 1.

Compound (I) (prepared as reported e.g. in WO96/37459) (0.5 g 0.84 mmol) and serinol (0.382 g; 4.19 mmol) are loaded in the jar filled with appropriate stainless steel balls as in example 1. The jar is then closed, inserted in the mill and subjected to a 650 rpm for 30 min. After cooling to room temperature, the crude reaction is collected from the jar with water and the obtained solution is neutralized with 2N HCl and analyzed by HPLC by means of an external standard.

Yield: 47%

Example 11

Preparation of the Intermediate (IX) by Mechanical Milling of Reactants

This intermediate compound (IX) is obtained by amidation of the substrate compound 2 with isoserinol, according to the following Scheme 5

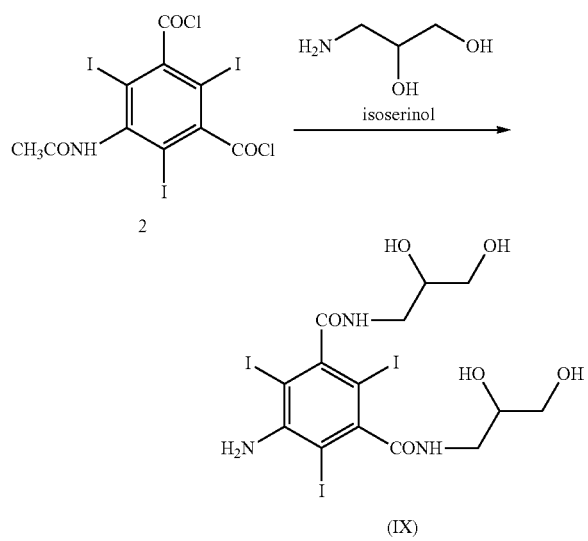

The amidation reaction was carried out in planetary ball mill PM100 (Retsch GmbH) equipped with stainless steel ball as in example 1.

Compound 2 (prepared as reported in WO98/54124) (0.64 g; 1 mmol) and isoserinol (0.46 g; 5 mmol) are loaded in the jar filled with appropriate stainless steel balls as in example 1. The jar is then closed, inserted in the mill and subjected to a 650 rpm for 30 min. After cooling to room temperature, the crude reaction is collected from the jar with water and the obtained solution is neutralized with 2N HCl and analyzed by HPLC by means of an external standard.

Yield: 53%

Example 12

Preparation of the Intermediate (X) by Mechanical Milling

This intermediate compound (X) is obtained by amidation of the substrate compound 3 with isoserinol, according to the following Scheme 6

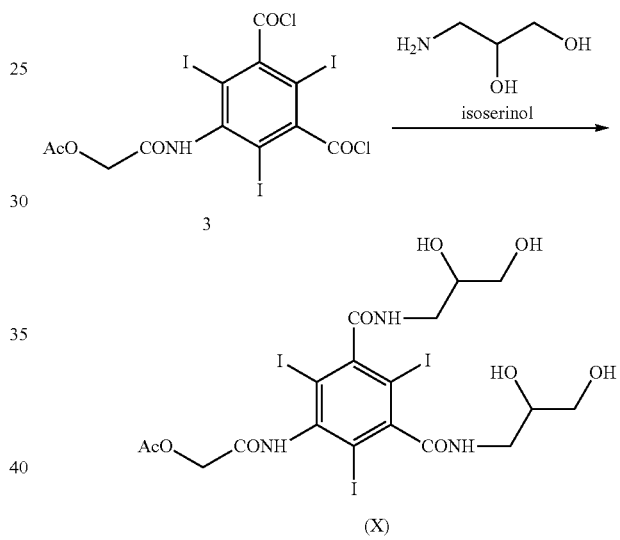

The amidation reaction was carried out in planetary ball mill PM100 (Retsch GmbH) equipped with stainless steel ball as in example 1.

Compound 3 (prepared as reported in U.S. Pat. No. 4,352,788) (0.7 g; 1 mmol) and isoserinol (0.46 g; 5 mmol) are loaded in the jar filled with appropriate stainless steel balls as in example 1. The jar is then closed, inserted in the mill and subjected to a 650 rpm for 30 min. After cooling to room temperature, the crude reaction is collected from the jar with water and the obtained solution is neutralized with 2N HCl and analyzed by HPLC by means of an external standard.

Yield: 51%

Comparative Data

Table 1 compares the molar ratios (compound (II) to serinol) and reaction times of experimental tests discussed in Examples 1-4 of WO00/15602 using a large excess of serinol to achieve Acetyl Iopamidol in the absence of any solvent, with corresponding molar ratios and reaction times used for tests of the above examples 1-3 where the same compound is obtained by mechanical co-milling of a mixture comprising only compound (II) and serinol.

TABLE 1

| | Substrate (II) | Serinol | Molar ratio | T (° C.) | t (h) | Yield (%) | Rpm |
|---|---|---|---|---|---|---|---|
| | | | WO00/15602 process | | | | |
| Example 1 | 0.179 mol | 1.49 mol | 8.3 | 48 | 58 | 78 | N.A. |
| Example 2 | 0.179 mol | 2.15 mol | 12 | 44 | 70 | 84 | N.A. |
| Example 3 | 0.179 mol | 2.87 mol | 16 | 48 | 48 | 90 | N.A. |
| Example 4 | 1.79 mol | 21.5 mol | 12 | 45 | 70 | 84.9 | N.A. |
| | | | Invention process | | | | |
| Example 1 | 1.4 mmol | 7 mmol | 5 | N.A. | 0.33 | 82 | 650 |
| Example 2 | 1.4 mmol | 7 mmol | 5 | N.A. | 0.67 | 89 | 650 |
| Example 3 | 1.4 mmol | 7 mmol | 5 | N.A. | 1.17 | 61 | 400 |

CONCLUSION

The data of Table 1 show that the solution provided by the present invention allows both a reduction of required amount of amine (per mole of compound (II)) and a significant reduction of the reaction time required to achieve the completion of the amidation reaction, thereby consenting an advantageous reduction in the overall cost of the industrial process.

The invention claimed is:

1. A process for preparing acetyl Iopamidol which comprises reacting compound (II) with serinol according to the scheme:

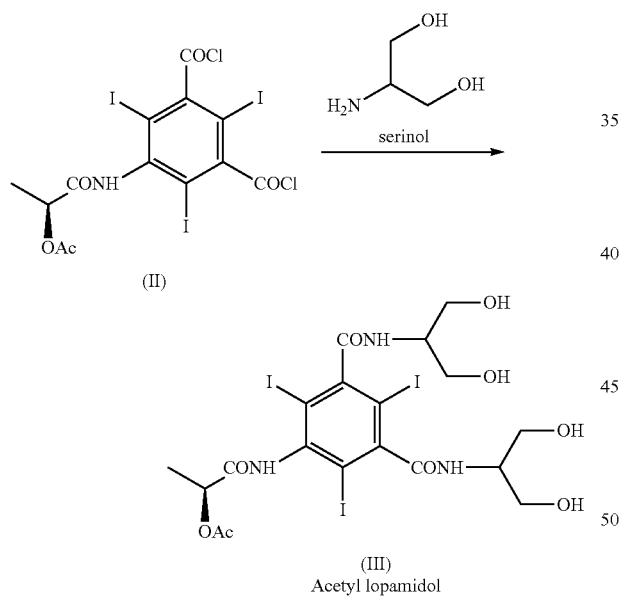

(III)
Acetyl Iopamidol wherein said process is carried out by mechanical co-milling of compound (II) and serinol.

2. The process according to claim 1 wherein serinol and compound (II) are used at a molar ratio of from 2:1 to less than 6:1.

3. The process according to claim 1 wherein the mechanical co-milling of compound (II) and serinol is carried out in the presence of a base.

4. The process according to claim 3 wherein the base is an organic base selected from triethanolamine and N-methylmorpholine.

5. The process according to claim 4 carried out by using from 2 to 5 moles of serinol for each mole of compound (II).

6. The process according to claim 5 wherein compound (II) and serinol are used at a molar ratio of from 1:2 to 1:3.

7. The process according to claim 4 wherein compound (II) and the base are used at a molar ratio of from 1:3 to 1:10.

8. The process according to claim 1, wherein the milling is carried out in a ball milling system at a rotation speed of from 400 to 1000 rpm.

9. The process according to claim 8 wherein the process is carried out at a reaction time of from 20 to 180 min.

10. The process according to claim 1 carried out in the presence of a volume of a lubricant ranging from 0.5 to 1.5 times the amount, by weight, of compound (II).

11. A process for the preparation of Iopamidol which comprises:
  a) obtaining acetyl Iopamidol by mechanical milling of compound (II) and serinol by use of the process according to claim 1
  b) converting the acetyl Iopamidol into Iopamidol by hydrolysis of the acetyl group and purification of the Iopamidol.

12. A process for the preparation of a compound of formula (V)

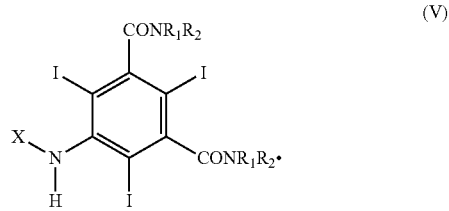

in which:
  $R_1$ is a $C_1$-$C_6$ alkyl substituted by one or more hydroxyl groups;
  $R_2$ is H or a $C_1$-$C_6$ alkyl optionally substituted by one or more hydroxyl groups; and
  X is selected from the group consisting of: H, Pg and —$COR_3$; where
    $R_3$ is a $C_1$-$C_6$ alkyl, optionally substituted by one or more groups selected from $C_1$-$C_4$ alkoxy and acetyloxy (—OAc) and,
  Pg is an amino protecting group;
which comprises:
  a) obtaining a 5-amino-2,4,6-triiodo-1,3-benzendicarboxylic acid dichloride of formula (VI)

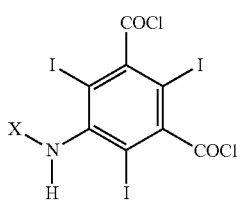

where X is as above defined for the compounds of formula (V), and b) reacting the obtained dichloride with an amine of formula $NHR_1R_2$ where $R_1$ and $R_2$ are as above defined, to give the corresponding diamide derivative;

wherein the step b) of the process is carried out according to the scheme

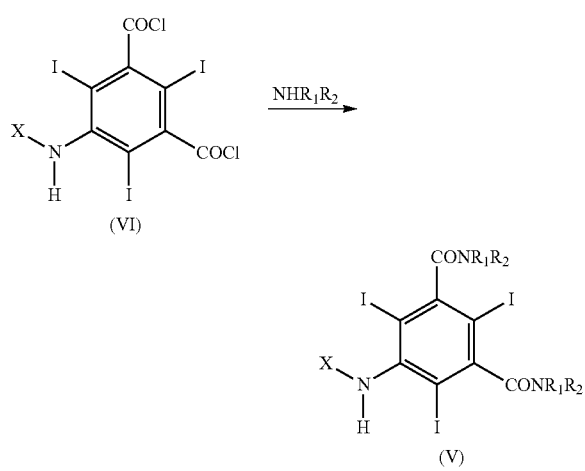

by mechanical co-milling of reactants.

13. The process according to claim 12 wherein in the compound of formula (V):

$R_1$ is a $C_1$-$C_3$ alkyl substituted by 1 or 2 hydroxyl groups;

$R_2$ is H, and

X is H or —$COR_3$, in which $R_3$ is a $C_1$-$C_3$ alkyl optionally substituted by one or more groups selected from acetyloxy (—OAc) and methoxy (—$OCH_3$).

14. The process according to claim 12 for the preparation of a compound of formula (V) selected from the compounds of formula:

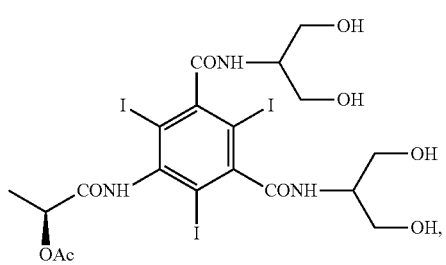

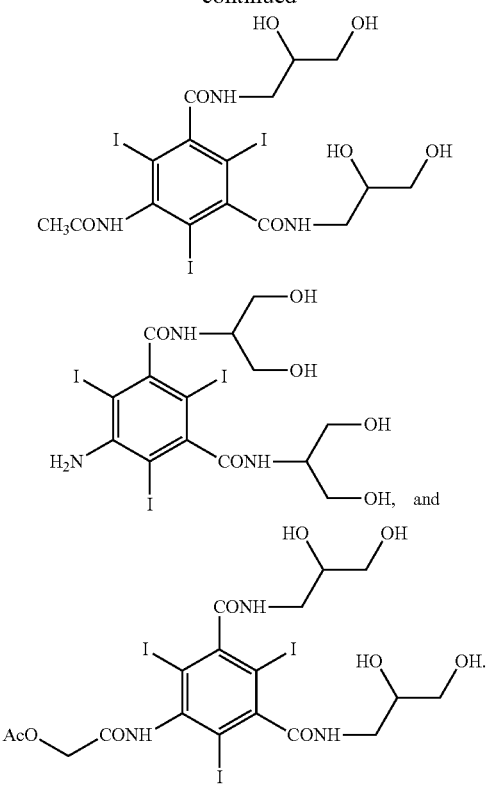

15. The process according to claim 11 wherein step a) is carried out in a ball milling system comprising a milling jar and wherein step b) of the process comprises converting the acetyl Iopamidol into Iopamidol directly in the milling jar, collecting the Iopamidol from the milling jar with water, and purifying the Iopamidol over an ion-exchange resin.

16. The process according to claim 11 for the preparation of Iopamidol, which is carried out according to the following synthetic Scheme 3:

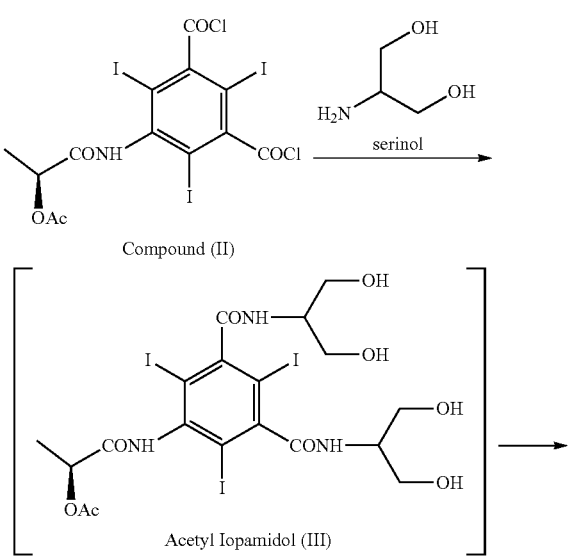

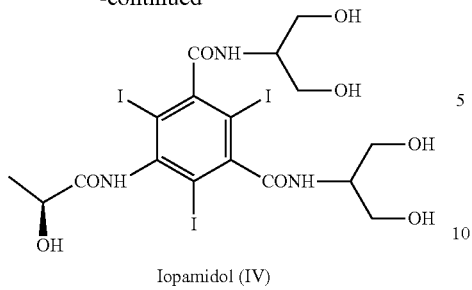
Iopamidol (IV)
and wherein step b) further comprises:
a') collecting the acetyl Iopamidol, and optional elution of the acetyl Iopamidol over an ion-exchange resin;
b') hydrolysis of the acetyl group under basic conditions;
c') purifying the Iopamidol over an ion-exchange resin; and
d') crystallization of the Iopamidol.
* * * * *